United States Patent [19]

Wong et al.

[11] 4,400,330
[45] Aug. 23, 1983

[54] METHOD FOR PREPARATION OF N-PHOSPHONOMETHYLGLYCINE

[75] Inventors: Rayman Y. Wong, Richmond; Nathan S. Bunker, El Cerrito, both of Calif.

[73] Assignee: Stauffer Chemical Company, Westport, Conn.

[21] Appl. No.: 403,239

[22] Filed: Jul. 29, 1982

[51] Int. Cl.$^3$ .............................................. C07F 9/38
[52] U.S. Cl. ............................. 260/502.5 F; 544/337
[58] Field of Search .................. 260/502.5 F, 502.5 E; 544/337

[56] References Cited

U.S. PATENT DOCUMENTS 2,959,590  11/1960  Moss ................................... 544/337
3,288,846  11/1966  Irani et al. ..................... 260/502.5 F
3,954,761   5/1976  Redmore ............................. 544/337
4,128,558  12/1978  Hendricks et al. .......... 260/502.5 E

FOREIGN PATENT DOCUMENTS 2528633  2/1976  Fed. Rep. of Germany ... 260/502.5 F

Primary Examiner—J. E. Evans
Attorney, Agent, or Firm—Paul R. Martin

[57] ABSTRACT

A method for the production of N-phosphonomethylglycine is disclosed which comprises the steps of:
(1) first reacting 2,5-diketopiperazine with p-formaldehyde, then adding substituted phosphorus compound, all in the presence of a low molecular weight carboxylic acid solvent, to form an intermediate bis-phosphonomethyl-2,5-diketopiperazine compound,
(2) isolating said intermediate compound,
(3) subsequently reacting said intermediate bis-phosphonomethyl-2,5-diketopiperazine compound with a hydrolyzing agent; and,
(4) thereafter acidifying said reactants with a mineral acid to form the end product, N-phosphonomethylglycine.

8 Claims, No Drawings

METHOD FOR PREPARATION OF N-PHOSPHONOMETHYLGLYCINE

BACKGROUND OF THE INVENTION

This invention relates to a novel method for the preparation of N-phosphonomethylglycine, a compound which is a known herbicide and plant growth regulator.

Herbicides are widely used by farmers, commercial agricultural companies, and other industries in order to increase crop yields for such stable crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are normally incorporated into the soil prior to the emergence of the weed plants from the soil, and the post-emergence herbicides are normally applied to plant surfaces after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxy acetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have been made to develop herbicides which are biodegradable into harmless residues within a relatively short time after their application.

One such compound, which has been found to be biodegradable, yet which is effective as a herbicide and plant growth regulator when employed at lower rates, is N-phosphonomethylglycine and various salts thereof. The N-phosphonomethylglycine and agriculturally effective salts have been approved for use by the U.S. Government, and, as a consequence, this herbicide has become extremely successful commercially.

The N-phosphonomethylglycine and certain salts are the only effective and approved post-emergence herbicides in the field. The present commercial compound is the isopropylamine salt of N-phosphonomethylglycine and derivatives thereof.

In field use it is normally applied in amounts of from 0.01 to about 20 pounds per acre, preferably from 2 to 6 pounds per acre.

The N-phosphonomethylglycines, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reaction products. Other methods include the phosphonomethylation of glycine and the reaction of ethyl glycinate with formaldehyde and diethylphosphite. The latter method is described in U.S. Pat. No. 3,799,758 (Franz, Mar. 26, 1974). In addition, there is a whole series of patents, relating to N-phosphonomethylglycines, their salts, and derivatives thereof, described as being useful herbicides and plant growth regulators. Such additional patents relating to the N-phosphonomethylglycines, methods of application, methods of preparation, salts, and derivatives, include U.S. Pat. No. 3,868,407, U.S. Pat. No. 4,197,254, and U.S. Pat. No. 4,199,354, among others.

Because of the importance of N-phosphonomethylglycine and certain salts as herbicide, other methods of making the compounds are constantly being sought in order to provide improved or alternate methods of manufacture.

The instant invention is thus concerned with a novel method for the production of N-phosphonomethylglycine compounds.

SUMMARY OF THE INVENTION

It has now been discovered that N-phosphonomethylglycine can be produced by reacting a diketopiperazine starting compound with formaldehyde and a substituted phosphorus compound in the presence of a low molecule weight carboxylic acid solvent to form an intermediate product, subsequently hydrolyzing that intermediate product with an alkali or alkaline earth base, and thereafter acidifying the product thus produced with a mineral acid to form the end product, N-phosphonomethylglycine.

In general, the process comprises the steps of:

(1) reacting, 2,5-diketopiperazine, a compound of the formula

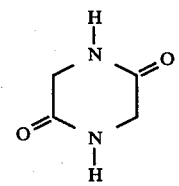

with p-formaldehyde and then adding to the reaction solution a substituted phosphorus compound of the formula PXYZ, wherein X is a halogen, and Y and Z are independently selected from the group consisting of halogens, said reaction being conducted in the presence of a low molecular weight carboxylic acid solvent, and at a sufficient temperature and for a sufficient period of time to cause formation of an intermediate compound, bis-phosphonomethyl2,5-diketopiperazine, (2) isolating said intermediate compound, (3) subsequently hydrolyzing said intermediate compound with an alkali or alkaline earth base to split the compound, and form an alkali or alkaline earth salt of N-phosphonomethylglycine, and (4) acidifying said salt of N-phosphonomethylglycine with a mineral acid to form N-phosphonomethylglycine.

The formula for the reactions set forth above, utilizing phosphorus trichloride, and acetic acid, along with the 2,5-diketopiperazine and p-formaldehyde can be represented as follows:

(1.) 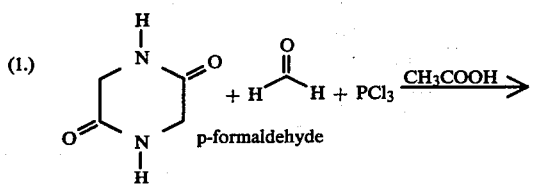

2,5-diketopiperazine     phosphorus trichloride

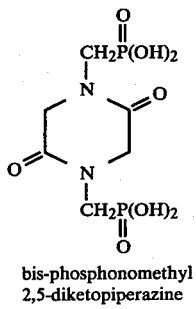

bis-phosphonomethyl 2,5-diketopiperazine

2. Isolation of bis-phosphonomethyl-2,5-diketopiperazine (3.) 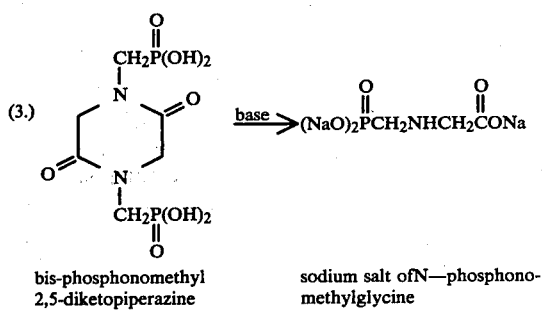

bis-phosphonomethyl 2,5-diketopiperazine     sodium salt of N—phosphonomethylglycine (4.) 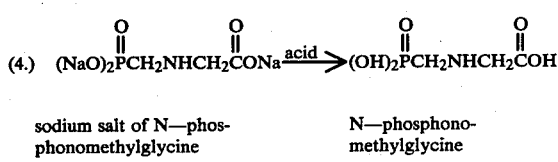

sodium salt of N—phosphonomethylglycine     N—phosphonomethylglycine

The reactions set forth in steps (1), (2), (3) and (4) above are preferably carried out in a conventional reaction vessel under such conditions of time, temperature, and pressure as to maximize yield. Preferably, in step (1), when acetic acid is the solvent used the temperature ranges from about 25° to about 122° C., and most preferably from about 116° to about 118° C. The reaction is normally carried out at atmospheric pressure.

In the reaction as set forth in step (1), the 2,5-diketopiperazine and p-formaldehyde are first reacted together, and the reaction solution brought to reflux temperature which is about 118° C. After a period of time, the solution is cooled to room temperature at which time phosphorus trichloride is added to the reaction solution. The entire solution is thereafter brought back to reflux temperature. The reason the phosphorus trichloride is added at room temperature is because when the phosphorus trichloride is added, a gas is given off, and were the phosphorus trichloride to be added at reflux temperature, a violent reaction could result. Therefore, the solution is first cooled to room temperature, and then after the phosphorus trichloride has been added, it is again returned to reflux temperature, of about 118° C.

The reactants are preferably reacted in step (1) of the process for a time ranging from about 120 to about 300 minutes, and most preferably from about 160 to about 200 minutes.

p-Formaldehyde, instead of ordinary formaldehyde solutions, is used in the process in order to exclude water from the reaction solution.

Phosphorus trichloride is the substituted phorphorus compound of choice, although phosphorus tribromide and other phosphorus trihalides can also be used.

Glacial acetic acid is the preferred low molecular weight carboxylic acid solvent, however, other low molecular weight carboxylic acids such as propanoic and butanoic acids can be used with substantially equivalent results.

The bis-phosphonomethyl-2,5-diketopiperazine formed in accordance with step (1) of the process of the invention, is isolated from the other reactants by adding water to the reaction solution. The reason for adding water is that one of the by-products of the first step of the process is bis-chloromethyl ether which is considered to be a carcinogen. In order to eliminate this by-product, it is necessary to add water which splits the compound into harmless residues. The bisphosphonomethyl-2,5-diketopiperazine can then be isolated by distilling off the solvent, leaving behind a residue of the desired intermediate product.

Step (3) of the reaction, in which the intermediate compound is reacted with an alkali or alkaline earth base hydrolyzing agent, is also preferably carried out in a conventional reaction vessel under such conditions of time, temperature, and pressure as to maximize yield. Preferably, in step (3), the temperature ranges from about 90° to about 110° C. and most preferably from about 95° to about 105° C. The reaction of step (3) is also normally carried out at atmospheric pressure.

The reaction time for step (3) at atmospheric pressure and at the indicated temperatures, is normally conducted for about 60 to about 1440 minutes, and most preferably from about 240 to about 600 minutes.

The hydrolyzing agent of choice in the third step of the process is sodium hydroxide, although other alkali or alkaline earth hydroxides can be used, such as potassium hydroxide, and calcium hydroxide.

Hydrochloric acid is the preferred mineral acid for use in acidifying the reactants in the fourth step of the process, however, any mineral acid such as sulfuric acid or hydriodic acid can be used.

The mole ratio of 2,5-diketopiperazine to p-formaldehyde to substituted phosphorus compound in the first step of the reaction can range from about 1:2.2:2.2 to about 1:2:2, with the preferred ratio being 1 mole of 2,5-diketopiperazne to 2 moles of p-formaldehyde to 2 moles of phosphorus trichloride.

The low molecular weight carboxylic acid is used for solvent purposes and it is preferred that an excess of this acid be present.

In step (3) of the reaction, the mole ratio of intermediate bis-phosphonomethyl-2,5-diketopiperazine to the preferred base sodium hydroxide can range from about 1:6 to about 1:10, with the preferred ratio being 1 mole of intermediate bis-phosphonomethyl-2,5-diketopiperazine compound to 6 moles of sodium hydroxide.

The 2,5-diketopiperazine starting compound can be commercially obtained from the Aldrich Chemical Company.

This invention will be better understood by reference to the specific example which follows, which is illustrative of the instant invention.

EXAMPLE 1

To a 500 milliliter (ml), four-necked, round-bottom flask equipped with an overhead stirrer, a condenser hooked to a caustic bath, a stopper, and an argon inlet, was added 10.0 grams (g) (0.09 mole) of 2,5-diketopiperazine, 5.3 g of p-formaldehyde, and 60 ml of glacial acetic acid. A white suspension formed and this suspension was heated to reflux and refluxed for approximately 45 minutes. A clear yellow solution then appeared, and this solution was cooled to room temperature while being stirred. To the stirred solution was added 24.1 g (0.18 mole) of phosphorus trichloride and it was observed that hydrogen chloride evolved during this procedure. The evolution continued over a period of approximately 5 minutes during the addition. When the addition was complete, the reaction mixture was heated to reflux again, during which time more hydrogen chloride evolved, and was then refluxed for 2.0 hours. A light orange slurry formed, and this slurry was cooled to room temperature and diluted with 150 ml of water (the purpose of this was to destroy any bis-chloromethyl ether which had formed) and the slurry was then heated to reflux and refluxed for 15 hours. The product was then dried in vacuo, and 0.3 g of the light orange residue was removed for sample purposes.

The bulk of the residue was then transferred to a 1000 ml, single-necked, round-bottom flask and dissolved in 350 ml of distilled water. The solution was stirred with a magnetic stirrer, and to the solution was added a solution of 35 g of sodium hydroxide dissolved in 150 ml of water. A clear yellow solution formed, and this solution was heated to reflux and then refluxed for 24 hours. Thereafter, the mixture was acidified to a pH of 1 with concentrated hydrochloric acid.

An aliquot was analyzed by nuclear magnetic resonsance and high pressure liquid chromatography and found to contain the subject compound, N-phosphonomethylglycine.

The N-phosphonomethylglycine compound produced in accordance with this method, in and of itself, has herbicidal and plant growth regulating efficacy. However, because the acid is not in itself very soluble in aqueous solutions, it is preferred to convert the compound to its salt form for inclusion into herbicidal compositions. Salt forms which have been found to have high rates of herbicidal activity and plant growth regulating activity are the trialkylsulfonium salts of N-phosphonomethylglycine, such as are disclosed in U.S. Pat. No. 4,315,765. These salts can be produced by reacting the N-phosphonomethylglycine with trialkylsulfonium hydroxide in accordance with the method disclosed in that patent.

It will be appreciated by those skilled in the art that variations in times, temperatures, pressures, and the like can be had in the method of the invention without departing from the spirit of the invention and the scope of the claims herein.

What is claimed is:

1. A method for the production of N-phosphonomethylglycine which comprises the steps of:
   (1) first reacting 2,5-diketopiperazine with p-formaldehyde, then adding a substituted phosphorus compound, of the formula PXYZ, wherein X is a halogen, and Y and Z are independently selected from the group consisting of the halogens, all in the presence of a low molecular carboxylic acid solvent, to form an intermediate bis-phosphonomethyl-2,5-diketopiperazine compound,
   (2) isolating said intermediate bis-phosphonomethyl-2,5-diketopiperazine compound,
   (3) reacting said intermediate bis-phosphonomethyl-2,5-diketopiperazine compound with a hydrolyzing agent selected from an alkali or alkaline earth base to form a salt of N-phosphonomethylglycine, and
   (4) acidifying said salt with a suitable mineral acid to cause formation of the end product, N-phosphonomethylglycine.

2. The method of claim 1 in which said substituted phosphorus compound is phosphorus trichloride.

3. The method of claim 1 in which said low molecular weight carboxylic acid is acetic acid.

4. The method of claim 1 in which the alkali or alkaline earth base is sodium hydroxide.

5. The method of claim 1 in which the reactants in step (4) are acidified with hydrochloric acid.

6. The method of claim 1 in which the reactants in step (1) are heated to a temperature ranging from about 25° to about 118° C.

7. The method of claim 1 in which the low molecular weight carboxylic acid is selected from the group consisting of acetic acid, propanoic acid, and butanoic acid.

8. The method of claim 2 in which the ratio of 2,5-diketopiperazine to p-formaldehyde to substituted phosphorus compound ranges from about 1:2:2 to about 1:1.2:1.2.

* * * * *